United States Patent [19]
Sigwart et al.

[11] Patent Number: 5,307,811
[45] Date of Patent: May 3, 1994

[54] FEMORAL COMPRESSION DEVICE

[75] Inventors: Ulrich Sigwart, London, England; Dan Akerfeldt, Uppsala, Sweden

[73] Assignee: Radi Medical Systems AB, Uppsala, Sweden

[21] Appl. No.: 712,413

[22] Filed: Jun. 10, 1991

[30] Foreign Application Priority Data

Jun. 11, 1990 [SE] Sweden .................. 9002077
Oct. 12, 1990 [SE] Sweden .................. 9003271

[51] Int. Cl.$^5$ .................................. A61B 5/02
[52] U.S. Cl. .................... 128/677; 128/668; 606/157
[58] Field of Search ........... 606/157, 158; 128/672, 128/677, 668, 637, 845, 846, 869

[56] References Cited

U.S. PATENT DOCUMENTS

| | | | |
|---|---|---|---|
| 1,953,466 | 4/1934 | Corwin | 128/677 |
| 2,493,406 | 5/1947 | Hicks, III | 128/96 |
| 3,040,737 | 6/1992 | Kompelien et al. | 128/637 X |
| 3,625,219 | 12/1991 | Abrams et al. | |
| 3,779,249 | 12/1973 | Semler | 128/325 |
| 4,182,338 | 1/1980 | Stanulis | 128/325 |
| 4,233,980 | 11/1980 | McRae et al. | 128/325 |
| 4,269,193 | 5/1981 | Eckerle et al. | 128/672 X |
| 4,509,528 | 4/1985 | Sabota | |
| 4,572,182 | 2/1986 | Royse | 128/325 |
| 4,742,825 | 5/1988 | Freund et al. | 128/325 |
| 4,770,175 | 9/1988 | McEwen | |
| 4,817,595 | 4/1989 | Maass | 128/155 |
| 4,829,994 | 5/1989 | Kurth | 128/96.1 |
| 4,924,871 | 5/1990 | Honeyager | 128/672 |
| 4,957,105 | 9/1990 | Kurth | 128/96.1 |
| 4,987,900 | 1/1991 | Eckerle et al. | 128/672 |
| 4,993,422 | 2/1991 | Hon et al. | 128/672 |
| 5,025,792 | 6/1991 | Hon et al. | 128/672 |

FOREIGN PATENT DOCUMENTS

| | | | |
|---|---|---|---|
| 120137 | 10/1984 | European Pat. Off. | 128/672 |
| 2529599 | 1/1983 | France | 128/672 |
| 12486 | of 1910 | United Kingdom . | |
| 21060 | of 1914 | United Kingdom . | |

Primary Examiner—Robert A. Hafer
Assistant Examiner—Sam Rimell
Attorney, Agent, or Firm—Foley & Lardner

[57] ABSTRACT

Femoral compression device including a pressurizing element for compressive bearing at the puncture site, preferably located at the femoral artery of a patient subjected to, for example, heart catheterization, and for applying a pressure on the same, and a base plate for supporting the pressurizing element. A belt is adapted to be fixed around the patient's body. The base plate has a top portion and a bottom portion and is adapted to be fixed to the belt and the pressurizing element is provided at the bottom portion of the base plate so as to exert a compressive force against the patient's body at the puncture site.

25 Claims, 4 Drawing Sheets

FEMORAL COMPRESSION DEVICE

BACKGROUND OF THE INVENTION

1. Field of the Invention

The present invention relates to a femoral compression device and a method for hemostasis of the femoral artery following, for example, catheterization. More particularly, the invention relates to a femoral compression device including a pressurizing means which presses on the femoral artery.

To be able to visualize arteries and veins with contrast medium during, for example, heart catheterization and angiography, one often enters via the femoral artery in the groin. Investigations via the femoral artery are especially difficult because of the high pressure against the artery wall. Today an investigation like that is performed by making a small incision in the femoral artery using a small diameter cannula. A guide is inserted into the cannula and into the artery, and thereafter a catheter is threaded over the guide into the artery. Thereafter the guide is removed and contrast medium is injected through the catheter into the artery.

After the investigation is completed, the catheter is withdrawn, leaving a wound, and the bleeding from the incision site in the femoral artery is stopped. This can be done manually, when, for example, the physician presses his finger against a compressive bandage laid on the wound for about 20 minutes. Obviously this is not a satisfactory method since it is inconvenient for both patients and physicians and also requires valuable physician time. Furthermore, it is difficult for the physician to maintain a constant pressure.

2. Discussion of the Related Art

Several devices have also been proposed by which a pressure is applied onto the wound in the femoral artery.

U.S. Pat. No. 4,509,528, issued May 9, 1985, to Sabota, describes a hemostat with a blood flow sensor. The sensor measures the blood flow and can be of, for example, the Doppler type. The signal from the sensor is processed by a signal processor, which in turn produces a second signal, preferably a sound, varying in volume in response to changes in the blood flow through the blood vessel. This arrangement is well known and described earlier. When the sound, and thus also the blood flow, varies, the latter is to be reset manually by a number of adjustments. Thus there exists no feed back from the sensor to the operating means.

U.S. Pat. No. 4,770,175, issued Sep. 13, 1988, to McEwen, describes a device for occluding, but not registering, blood flow into a digit. The device is provided with a pressurizing means and a sensor sensing the pressure exerted by the pressurizing means against the digit. The signal from the sensor is digitally processed and thereafter a signal goes to the pressurizing means in such a way that a constant, occluding pressure always acts on the digit. Thus the device does not include a sensor measuring blood flow. The Doppler device illustrated in the patent is only used to obtain standard curves to establish occluding pressure levels for different cuff and digit dimensions.

In U.S. Pat. No. 3,625,219, issued Dec. 12, 1991, to Abrams, et al., there is shown a device for hemostasis in which an inflatable balloon is used as pressurizing means. However this device involves a complex and unstable construction and does not allow patient movement. Like the above devices, this one does not comprise a feed back from the sensor to the pressurizing means.

The principle of these devices is the same: a pressure is applied on the incision site in the femoral artery for about 20 minutes following completed catheterization. The pressure is to be set high enough to stop bleeding but not so high that the blood flow is cut off down to the leg and foot.

Following balloon dilatation of the femoral artery in the leg it is especially important not to apply too high a pressure on the incision site as there is a risk that the dilated stenosis in the artery will contract if the blood pressure is too low. To avoid blood clots, the patients are given anti-coagulating agents, such as heparin, prior to the treatment. This of course extends the time required to stop the bleeding after having completed the procedure. For patients already taking heparin for medical reasons, the time will be as long as up to 1.5 hours. However, if insufficient pressure is applied, hematoma is a common side effect.

SUMMARY OF THE INVENTION

Therefore the object of the present invention is to provide a femoral compression device which is more reliable than and avoids the disadvantages of prior art.

Another object is to provide a device which is more comfortable and gives greater freedom of movement for the patient.

These objects are achieved by a femoral compression device according to the characterizing part of claim 1 and a method for hemostasis of the femoral artery following, for example, heart catheterization according to the characterizing part of claim 20 respectively.

BRIEF DESCRIPTION OF THE DRAWINGS

The invention will now be described with further detail below with reference to the accompanying drawings, in which.

DETAILED DESCRIPTION OF THE PREFERRED EMBODIMENTS

Figure 1:
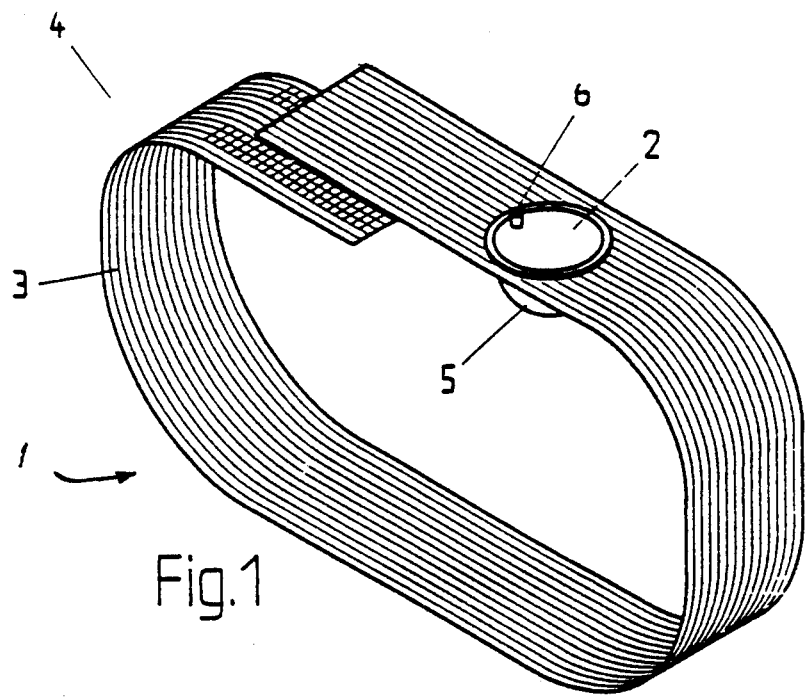
FIG. 1 is a schematic view of the femoral compression device according to the invention.

FIG. 1 shows a femoral compression device 1 comprising a pressurizing means 5 for compressive bearing at the puncture site, preferably located at the femoral artery of a patient subjected to, for example, heart catheterization, and for applying a pressure on the same, and a base plate 2 for supporting said pressurizing means. The device 1 comprises a belt 3 adapted to be fixed around the patient's body. The base plate 2 has a top portion and a bottom portion and is adapted to be fixed to the belt 3. The pressurizing means 5 is provided at the bottom portion of the base plate 2 so as to exert a compressive force against the patient's body at the puncture site. The base plate 2 can be integrated with the belt 3 as shown in FIG. 1. The base plate 2 is made of hard plastic or metal and is intended to be secured over the femoral puncture site of the treated patient by the flexible belt 3 enclosing the body of the patient at the hip area. The belt 3 is locked by a locking device 4; in the embodiment illustrated this is of interlocking tape sold as VELCRO tape. On the lower side of the base plate 2, the pressurizing means 5 is a pressure tight arrangement in the form of a semi-spherical balloon. The material of the balloon 5 should have maximum flexibility and minimum creep. The balloon 5 is preferably made of a soft plastic, elastomer or mixture thereof and is optionally reinforced, for example, with fabric. The plastic can be of PVC, being easily resilient with a constant inner overpressure, or of film sold under the trademark MYLAR, being only slightly resilient with a constant inner overpressure. In the embodiment illustrated, the base plate is circular, however, it can of course also take other forms, for example, square, rectangular or oval. A connection 6 is included in the top portion of the base plate 2 for inflating the balloon 5. To enable visual observation of bleeding at the puncture site, the balloon and a part of or the whole base plate 2 are made of transparent material (illustrated in FIG. 4). The base plate 2 can be integrated in the belt 3 or may be a separate unit.

Figure 2:
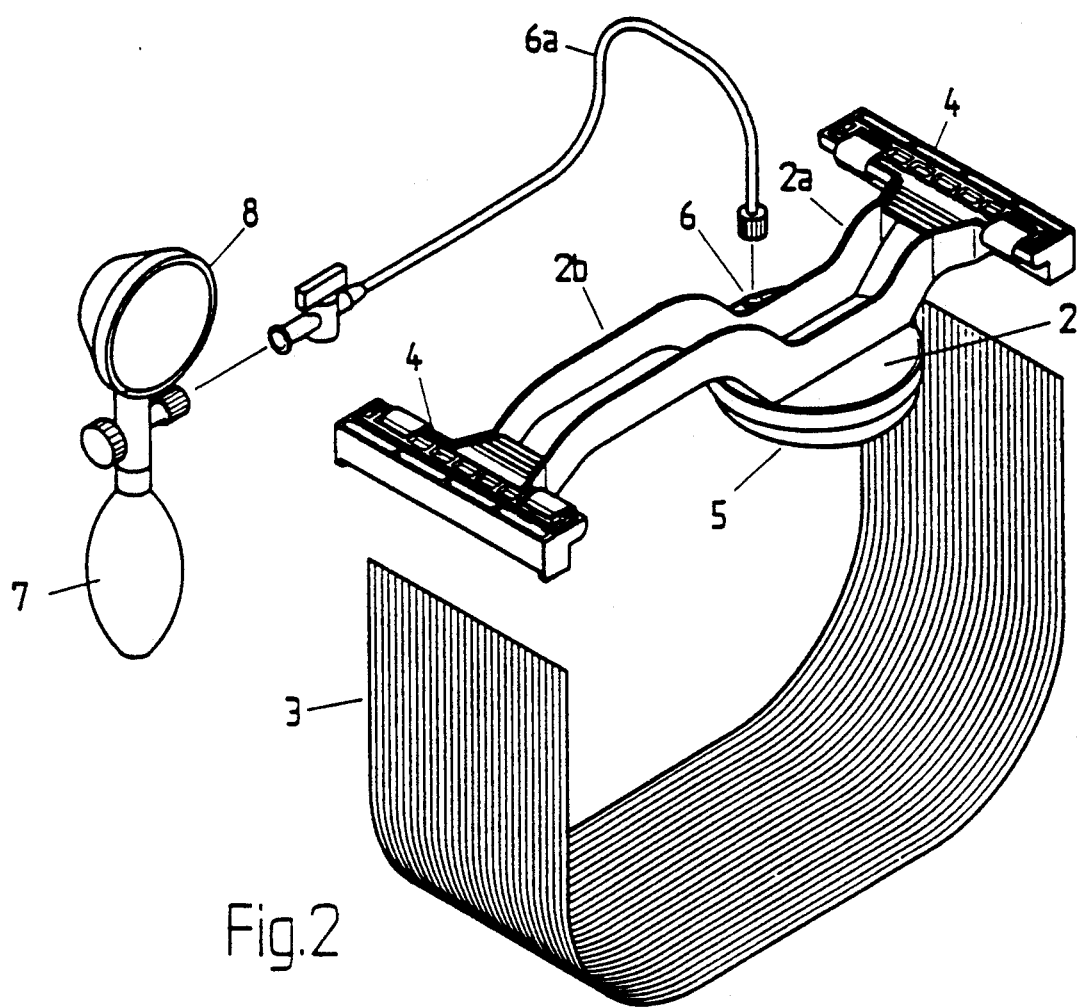
FIG. 2 shows an alternative embodiment of the femoral compression device.

FIG. 2 shows a preferred embodiment of the present invention. The features that differ in this embodiment from the embodiment described in connection with FIG. 1 are that the top portion of the base plate 2 comprises extension means 2a, 2b extending in opposite directions and being provided with locking means 4 in the ends thereof for insertion of a respective end of the belt 3. One extension 2a is shorter than one other extension 2b, the extensions preferably being arc shaped and disposed at an elevated position in relation the base plate 2. A balloon 5 is fastened in the bottom side of the base plate 2 in the same manner as in FIG. 1. A belt 3 is fastened in the outer ends of the extensions 2a, 2b by a self locking device 4 having a greater width than the extensions 2a, 2b. The width of the locking means generally corresponds to the width of belt 3, which is broad enough to compensate for imbalance of the device. Imbalance is also compensated for by the extended shape of the base plate 2 in that it gives the balloon 5 a stable base. This embodiment is especially comfortable for the patient as it allows some movement of the patient without changing the balloon position. Furthermore, the device can be left on the patient after completed hemostasis, in lieu of a conventional compressive bandage. In this figure there is also shown a tubing 6a connecting the connection 6 to a pump 7 having a pressure gauge 8.

Figure 3:
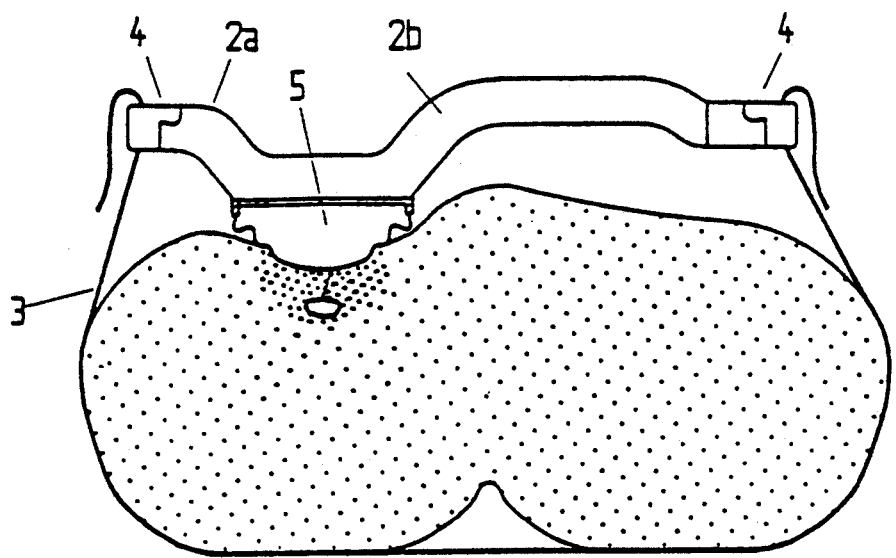
FIG. 3 is a sectional view of the femoral compression device according to FIG. 2, applied on a patient.
Figure 6B:
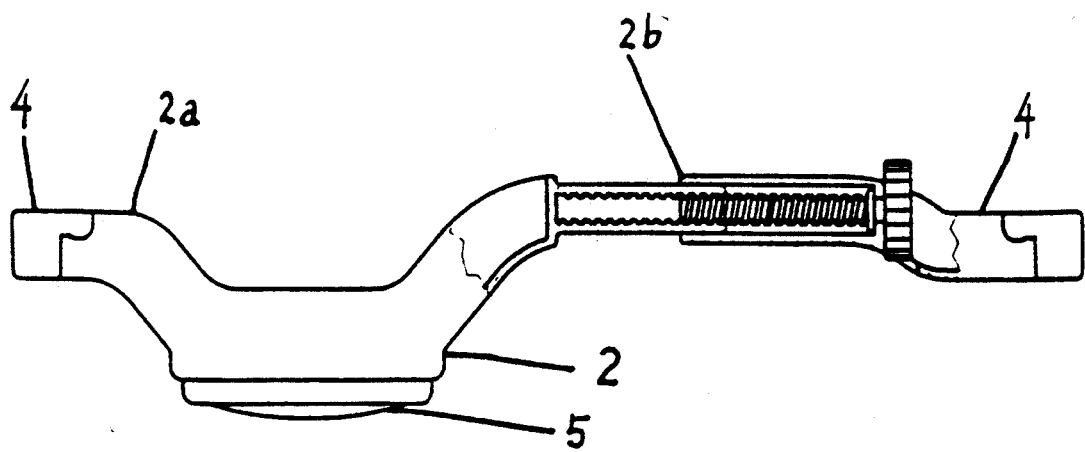
FIGS. 6a-6b are partial sectional views of the femoral compression device, including a telescopic extension.
Figure 6A:
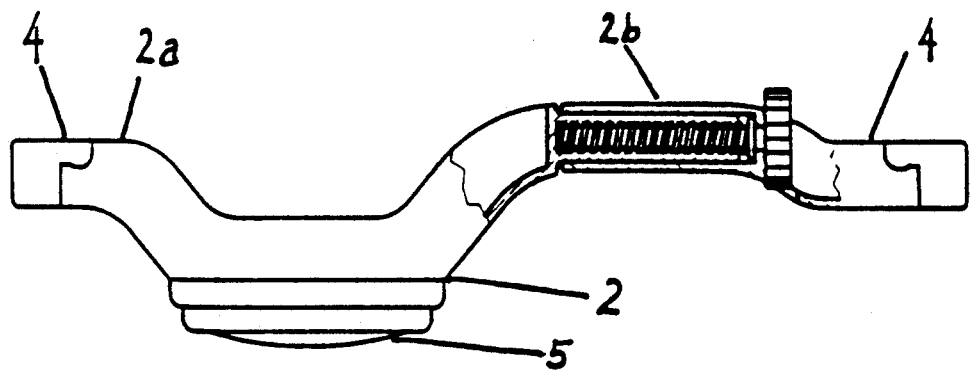
Figure 7:
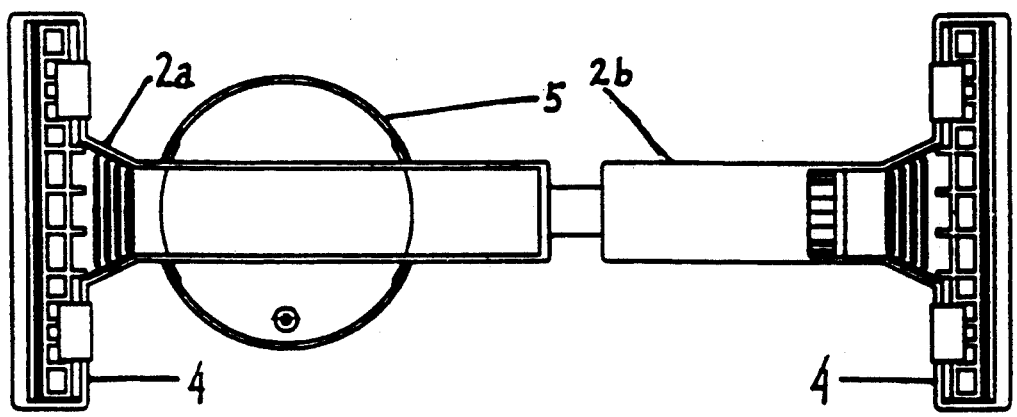
FIG. 7 is a plan view of the femoral compression device according to FIGS. 6a-6b.

The cross section according to FIG. 3 shows the device according to FIG. 2 mounted on a patient. As illustrated, the arc shaped extensions 2a, 2b provide clearance beneath the device, and this design makes the device more comfortable for fat patients. The short extension 2a is to be put on the artery side of the patient and the longer extension 2b on the other side of the patient. Alternatively, as shown in FIG. 6a-6b and 7, the base plate 2 is telescopically designed, enabling it to be adjusted to different body widths.

Figure 8:
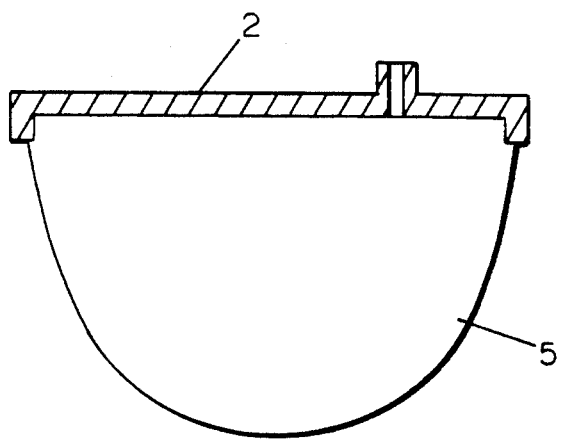
FIG. 8 is a sectional view of one embodiment of the pressurizing means.

The pressurizing means 5 can also be designed as a truncated cone, illustrated in FIG. 8, to decrease the surface pressed against the body. To obtain an even more selective pressure on a small surface, the surface pressed against the body is provided as a stiff portion, for example ten times thicker than the rest of the pressurizing means 5. This latter embodiment will function as a pneumatic air cylinder.

Furthermore, the pressurizing means can be provided with accordion folds in the upper portion closest to the base plate 2 to increase the effective stroke length thereof. This also eliminates the risk that the partially inflated balloon will be folded at the surface pressed against the skin, which during continued expansion of the balloon results in friction and therefore possible discomfort for the patient.

Following completed catheterization via the femoral artery, the balloon 5 is laid against the puncture site and tightened against the site by tightening the belt 3 and securing it by the locking device 4. The balloon 5 is inflated by the pump 7 via the connection 6 and tubing 6a to a pressure being at a determined value between the diastolic and systolic pressure level read on a pressure gauge 8. A tissue pressure is exerted on the artery which is slightly lower than the systolic pressure, and which results in maintaining the correct blood flow. The inflation of the balloon 5 can be done manually as in FIG. 2 or automatically as described below. The blood flow down to the leg and foot can be registered by measuring the pulse downstream of the puncture site. If the pressure is too low, blood will ooze out of the puncture site, as observed through the transparent balloon 5 and base plate 2.

Figure 4:
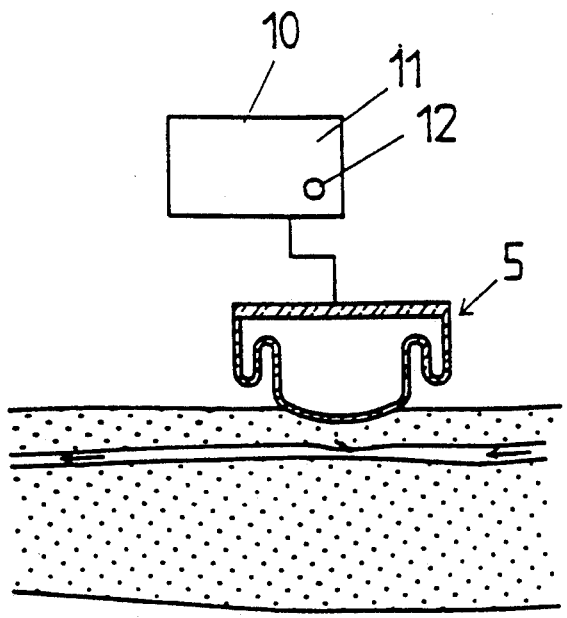
FIG. 4 is a schematic view of the femoral compression device, including an electronic control unit.

FIG. 4 shows the femoral compression device in association with an electronic control unit 10 comprising a driving means, such as a pump. Optionally the electronic control unit can be provided with a pressure gauge. This embodiment is constructed as an automatic regulating device in which, for example, selected pressure values and times can be programmed into the electronic control unit 10 for sequentially applying different pressures on the artery. After about 20 minutes, for example, the initial hemostasis pressure must be decreased. The automatic regulating device gives extra security in case the nursing personnel are absent at that time. The automatic regulating device also compensates for any creep relaxation in the plastic of the balloon 5 and any leakage in the system. The degree of inflation of the balloon 5 is controlled pneumatically or hydraulically via the driving means. Filling and emptying of the balloon 5 results in the balloon being pressed against and being eased from the puncture site, respectively.

The method according to the invention for hemostasis of the femoral artery of a patient following, for example, heart catheterization, comprises the steps of: applying a reference pressure over the puncture site; applying an additional pressure over the puncture site; monitoring the sum of the reference pressure and the additional pressure; gradually reducing the additional pressure over a prolonged period of time; and releasing the reference pressure when the hemostasis is fully completed.

In an alternative embodiment one also registers the pulsations of the pressure medium in the balloon 5 created by the pulse of the patient. The pulsations occur only between the systolic and diastolic pressure values. If no pulse can be registered, indicating that the blood flow through the artery is too high or too low, the electronic control unit 10 triggers an alarm calling for the attention of the nursing personnel. This embodiment guarantees that the balloon always is correctly positioned.

In a modification of the above embodiment, the pulsations in the pressure medium of said pressurizing means 5 caused by the pulse of the patient are registered and processed by the electronic control unit 10. The driving means is responsive to signals from the electronic control unit 10 in such a way that the selected pressure value is constantly maintained or updated, dependent on the registered pulsation value. Thus, this embodiment provides a feed-back from the pressurizing means to the electronic control unit. In the method according to this embodiment, the monitoring step further comprises registration of pulsation values caused by the patient's pulse at the puncture site, comparing the pulsation values with selected values and controlling the additional pressure dependent on the registered pulsation values.

Figure 5:
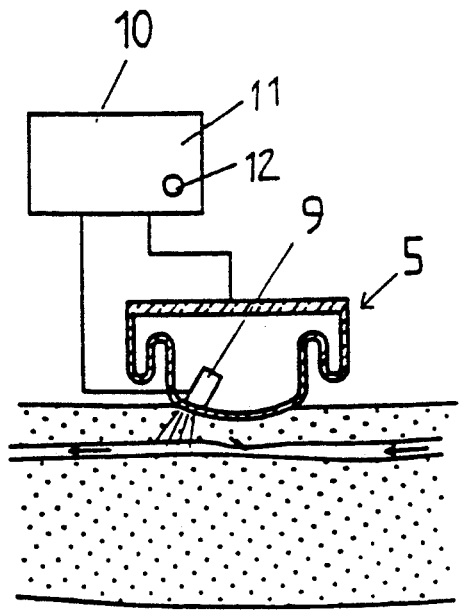
FIG. 5 is a schematic view of the femoral compression device, including an electronic control unit and a sensor.

In the embodiment shown in FIG. 5, an external sensor 9 disposed at or downstream of the compression site detects actual blood pressure in the artery and reports the detected actual blood pressure values to the electronic control unit 10 for comparison with a selected pressure value. The driving means is responsive to signals from the electronic control unit 10 in such a way that the selected pressure value is constantly maintained or updated dependent on the detected actual blood pressure value. In the method according to this embodiment, the monitoring step further comprises registration of actual blood pressure values at or downstream of the puncture site and comparing the actual blood pressure values with selected values and controlling the additional pressure dependent on the registrated actual blood pressure values.

The position of the sensor 9 is not critical, but should be at or downstream of the actual pressure site; naturally, it need not be disposed within the pressurizing means 5 but can also be arranged separately. Data from the sensor 9 can be read on a monitor 11, which is also provided with speakers (not shown) which sound an alarm if the flow is too high because the pressurizing means 5 has been moved out of position. The flow can also be adjusted manually in emergency cases by an adjusting wheel 12 on the monitor 11.

The sensor 9 can be a microphone detecting a Korotkoff-sound, which is the sound created by turbulence in arteries when the pressure applied is between the systolic and diastolic pressure levels of the patient, or an ultrasonic Doppler detecting the blood flow. However, sensors for measuring blood flow, such as the Doppler devices existing today, cannot be used to satisfactorily perform hemostasis of the femoral artery because of the femoral artery's deep position and the low blood flows therein.

When setting the pressurizing means 5 against the compression site, the groin skin and underlaying femoral artery, the pressurizing means is pushed downwardly until the sensor 9 detects the systolic pressure level, for example, using the Korotkoff-sound. Thereafter the electronic control unit regulates the applied pressure to a determined value under the systolic pressure in a certain number of percent units. This pressure level is updated or maintained constantly and the method according to the invention regulates independently of the absolute pressure values of the patient.

Optionally there is also arranged an optic sensor (illustrated schematically) which senses if bleeding starts and sends signals to the electronic control unit 10. The reflectance from the skin is detected by a light source and a detector. The optic sensor operates at two wave lengths, one that detects blood on the skin, and another that detects if the patient becomes blue as a result of a bleeding beneath the skin. Any color changes of the skin result in an alarm sound in the speakers, controlled by the electronic control unit 10.

We claim:
1. Femoral compression device comprising:
 (a) a pressurizing means for compressive bearing at a puncture site at a femoral artery of a patient, and for applying a pressure on the puncture site, having a transparent portion to permit viewing of the puncture site;
 (b) a belt adapted to be fixed around the patient's body; and
 (c) a base plate supporting the pressurizing means, including a top portion having a plurality of extensions, including first and second extensions extending in opposite directions, disposed at an elevated position in relation to the top portion of the base plate, and provided with locking means in the ends thereof for insertion of an end of the belt; a bottom portion connected to the pressurizing means; the base plate having a transparent portion to permit viewing of the puncture site.

2. Femoral compression device according to claim 1, wherein the first extension is shorter than the second extension 3. Femoral compression device according to claim 1, wherein the extensions of the base plate are telescopic.

4. Femoral compression device according to claim 1, wherein the locking means has a width which generally corresponds to a width of the belt.

5. Femoral compression device according to claim 1, wherein the top portion of the base plate is provided with a connection for connecting a tube to a means for generating a controlled pressure to the pressurizing means.

6. Femoral compression device according to claim 1, wherein the pressurizing means is in the shape of a semi spherical balloon.

7. Femoral compression device according to claim 1, wherein the pressurizing means is in the shape of a truncated cone.

8. Femoral compression device according to claim 7, wherein the truncated cone includes a pressure surface which is stiffer than the remainder of the pressurizing means.

9. Femoral compression device according to claim 1, wherein the pressurizing means and at least a part of the base plate is made of a transparent material.

10. Femoral compression device according to claim 1, wherein the pressurizing means includes an upper portion closest to the base plate having at least one accordion fold, to increase an effective stroke length of the pressurizing means.

11. Femoral compression device according to claim 1, further comprising an optic sensor for reading of a possible bleeding at the puncture site.

12. Femoral compression device according to claim 1, further comprising an electronic control unit provided with a means for driving the pressurizing means.

13. Femoral compression device according to claim 12, wherein the driving means is a pump.

14. Femoral compression device according to claim 12, wherein a plurality of selected pressure values and times are programmed into the electronic control unit for sequentially applying different pressures on the artery, whereby the driving means drives the pressurizing means in accordance with the programmed values.

15. Femoral compression device according to claim 14, wherein the pressurizing means includes a pressure medium having a pulsation responsive to a pulse of the patient, wherein the pulsations are registered and processed by the electronic control unit, the electronic control unit generating an alarm if the pulsations are absent.

16. Femoral compression device according to claim 12, wherein a pulse of the patient creates a plurality of pulsations in the pressure medium of the pressurizing means, wherein the pulsations are registered and processed by the electronic control unit, and wherein the driving means is responsive to a signal from the electronic control unit in such a way that the selected pressure value is constantly maintained or updated, dependent on the registered pulsations.

17. Femoral compression device according to claim 12, further comprising a sensor disposed at or downstream of the compression site which detects actual blood pressure in the artery and reports the detected actual blood pressure to the electronic control unit for comparison with a selected pressure value, and wherein the driving means is responsive to a signal from the electronic control unit (10) in such a way that the selected pressure value is constantly maintained or updated, dependent on the detected actual blood pressure.

18. Femoral compression device according to claim 17, wherein the sensor is a microphone detecting the Korotkoff-sound.

19. Femoral compression device according to claim 1, wherein the extensions are arc-shaped.

20. Method for achieving hemostasis of the femoral artery of a patient, comprising the steps of:
    applying a reference pressure over a puncture site in the femoral artery;
    applying an additional pressure over the puncture site;
    monitoring a sum of the reference pressure and the additional pressure;
    gradually reducing the additional pressure; and
    releasing the reference pressure when the hemostasis is fully completed;
    wherein the monitoring step further comprises registering a plurality of pulsation values caused by the patient's pulse at the puncture site, comparing the pulsation values with selected values, and controlling the additional pressure dependent on the pulsation values.

21. Method for achieving hemostasis of the femoral artery of a patient, comprising the steps of:
    applying a reference pressure over a puncture site in the femoral artery;
    applying an additional pressure over the puncture site;
    monitoring a sum of the reference pressure and the additional pressure;
    gradually reducing the additional pressure; and
    releasing the reference pressure when the hemostasis is fully completed;
    wherein the monitoring step further comprises registering a plurality of actual blood pressure values at or downstream of the puncture site, comparing the blood pressure values with a plurality of selected values, and controlling the additional pressure dependent on the blood pressure values.

22. Method for achieving hemostasis of the femoral artery of a patient, comprising the steps of:
    applying a reference pressure over a puncture site in the femoral artery;
    applying an additional pressure over the puncture site;
    monitoring a sum of the reference pressure and the additional pressure;
    gradually reducing the additional pressure;
    releasing the reference pressure when the hemostasis is fully completed; and
    selecting and programming selected pressure values and times into an electronic control unit, and sequentially applying different pressures on the artery in accordance with the pressure values.

23. Method according to claim 22, further comprising the steps of registering and processing a plurality of pulsations caused by the pulse of the patient, and triggering an alarm if the pulsations are absent.

24. Method according to claim 22, further comprising the steps of registering and processing a plurality of pulsations caused by the pulse of the patient, and, responsive to signals from said electronic control unit, constantly maintaining or updating the selected pressure value dependent on the registered pulsation value.

25. Femoral compression device according to claim 22, further comprising the steps of disposing a sensor disposed at or downstream of the compression site, detecting actual blood pressure in the artery, reporting the detected actual blood pressure to the electronic control unit for comparison with a selected pressure value, and, responsive to signals from the electronic control unit, maintaining or updating the selected pressure value dependent on the detected actual blood pressure.

* * * * *